(12) United States Patent
Pelletier et al.

(10) Patent No.: US 10,175,165 B2
(45) Date of Patent: Jan. 8, 2019

(54) MULTI-CHARACTERISTIC INTEGRATED COMPUTATIONAL ELEMENT USING LIGHT INCIDENCE ANGLE MANIPULATION

(71) Applicant: Halliburton Energy Services, Inc., Houston, TX (US)

(72) Inventors: Michael T. Pelletier, Houston, TX (US); Li Gao, Katy, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/107,381

(22) PCT Filed: Feb. 28, 2014

(86) PCT No.: PCT/US2014/019475
§ 371 (c)(1),
(2) Date: Jun. 22, 2016

(87) PCT Pub. No.: WO2015/130307
PCT Pub. Date: Sep. 3, 2015

(65) Prior Publication Data

US 2016/0341658 A1    Nov. 24, 2016

(51) Int. Cl.
| | | |
|---|---|---|
| *G01N 21/25* | (2006.01) | |
| *G01N 21/31* | (2006.01) | |
| *G01J 3/28* | (2006.01) | |
| *G01J 3/12* | (2006.01) | |
| *G01N 21/35* | (2014.01) | |

(52) U.S. Cl.
CPC ........... *G01N 21/31* (2013.01); *G01J 3/28* (2013.01); *G01J 2003/1226* (2013.01); *G01N 21/35* (2013.01)

(58) Field of Classification Search
CPC ........ G01J 3/26; G01J 3/02; G01J 3/51; G01J 9/00; G01N 21/255
USPC ......................................................... 356/416
See application file for complete search history.

(56) References Cited

U.S. PATENT DOCUMENTS

| | | |
|---|---|---|
| 6,798,518 B2 | 9/2004 | Digoggio et al. |
| 6,960,849 B1 | 11/2005 | Klody et al. |
| 7,262,920 B2 | 8/2007 | Unno et al. |
| 8,172,412 B2 | 5/2012 | Solyar et al. |
| 2004/0036940 A1* | 2/2004 | Hazelton ............. G03F 7/70266 359/223.1 |
| 2006/0052963 A1* | 3/2006 | Shkarlet ................. G01F 1/668 702/108 |
| 2011/0108719 A1 | 5/2011 | Ford et al. |

(Continued)

FOREIGN PATENT DOCUMENTS

WO    WO 2014/112974 A1    7/2014

OTHER PUBLICATIONS

International Search Report and the Written Opinion of the International Search Authority, or the Declaration, dated Jun. 10, 2014, PCT/US2014/019475, 12 pages, ISA/US.

(Continued)

*Primary Examiner* — Md M Rahman
(74) *Attorney, Agent, or Firm* — Haynes and Boone, LLP

(57) ABSTRACT

Multi-characteristic detection is achieved by altering the light incidence angle of a single Integrated Computational Element ("ICE") used in an optical computing device.

20 Claims, 9 Drawing Sheets

(56) References Cited

U.S. PATENT DOCUMENTS

| | | | |
|---|---|---|---|
| 2012/0150451 A1* | 6/2012 | Skinner | G01N 33/2823 |
| | | | 702/24 |
| 2013/0017610 A1 | 1/2013 | Roberts et al. | |
| 2013/0032334 A1* | 2/2013 | Freese | E21B 43/26 |
| | | | 166/250.01 |
| 2013/0284894 A1 | 10/2013 | Freese et al. | |
| 2013/0286398 A1* | 10/2013 | Freese | G01N 21/59 |
| | | | 356/432 |
| 2013/0338506 A1* | 12/2013 | Kim | G01S 7/52095 |
| | | | 600/447 |

OTHER PUBLICATIONS

Simcock, et al., "Precision in Imaging Multivariate Optical Computing," Optical Society of America, Applied Optics, Mar. 1, 2007, vol. 46, No. 7, pp. 1066-1080.

* cited by examiner

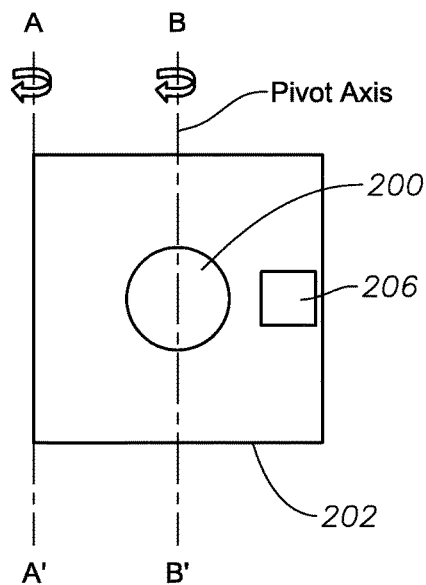
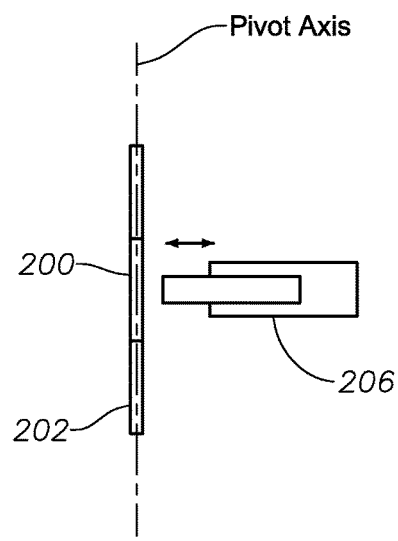
FIG. 2A  FIG. 2B
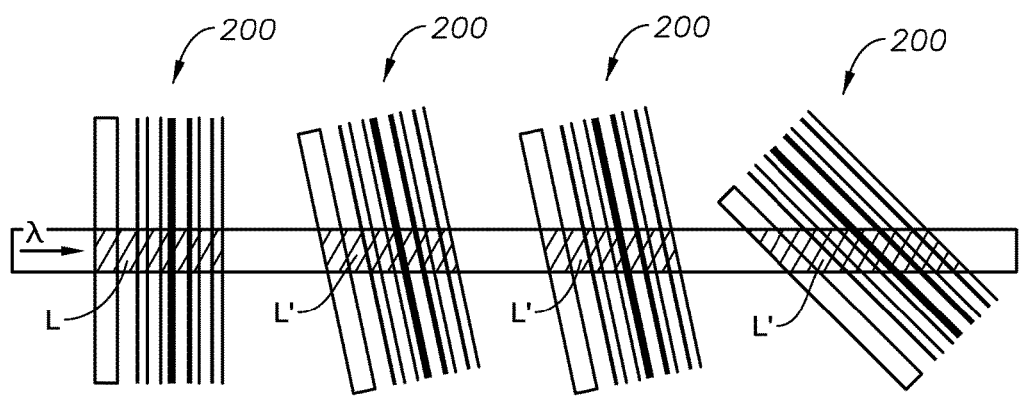
FIG. 3A   FIG. 3B   FIG. 3C   FIG. 3D

MULTI-CHARACTERISTIC INTEGRATED COMPUTATIONAL ELEMENT USING LIGHT INCIDENCE ANGLE MANIPULATION

PRIORITY

The present application is a U.S. National Stage patent application of International Patent Application No. PCT/US2014/019475, filed on Feb. 28, 2014, the benefit of which is claimed and the disclosure of which is incorporated herein by reference in its entirety.

FIELD OF THE DISCLOSURE

Embodiments of present disclosure generally relate to optical computing devices and, more particularly, to a multivariate optical computing device that alters the light incidence angle of an Integrated Computational Element to thereby detect a plurality of sample characteristics.

BACKGROUND

In recent years, optical computing techniques have been developed for applications in the oil and gas industry in the form of optical sensors on downhole or surface equipment to evaluate a variety of fluid properties. In general, an optical computing device is a device configured to receive an input of electromagnetic radiation from a sample and produce an output of electromagnetic radiation from a processing element, also referred to as an optical element, wherein the output reflects the measured intensity of the electromagnetic radiation. The optical computing device may be, for example, an Integrated Computational Element ("ICE"). One type of an ICE is an optical thin film optical interference device, also known as a multivariate optical element ("MOE").

Fundamentally, optical computing devices utilize optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE and one or more detectors, is capable of extracting the information of one or multiple characteristics/analytes within a substance and converting that information into a detectable output signal reflecting the overall properties of a sample. Such characteristics may include, for example, the presence of certain elements, compositions, fluid phases, etc. existing within the substance.

Currently, ICEs are assessed by applying an ICE regression vector to a single set of calibration data (i.e., spectral data set) to evaluate a performance factor, for example but not limited to, a standard error of calibration ("SEC"). This procedure is performed on a set of spectral data that describes a single chemical system that contains one or more components: its target characteristic/analyte and the remaining components (including spectral interferents), usually referred to the matrix. A subset of the chemical system can be used for validation purposes to calculate the performance factor, for example, the standard error of validation; this subset represents the same chemical system and the calibration set. An illustrative ICE can be constructed as a series of alternating layers of high and low refractive index materials with associated thicknesses deposited onto an optical substrate. Such a device has an optical transmission function (T), designed by assessing a performance factor (e.g. SEC) and using a minimization function to adjust the layer thicknesses to design an ICE with an optimal performance factor (e.g. low SEC), which is thus as predictive as possible.

As stated, illustrative ICEs can be made of multiple layers of at least two materials having different complex indices of refraction. The ICEs are normally employed at fixed angle of incidence relative to the electromagnetic radiation optical path. For example, the ICE can be arranged in an optical system to allow the electromagnetic radiation to strike the ICE at a 90 degree angle, or normal to its surface. The ICE is designed to achieve the desired transmission or reflection spectroscopic profile, by considering the substrate, the complex indices of refraction of the materials, the number of layers and the thicknesses of the layers to detect a desired characteristic, such as gas/oil ratio ("GOR"), C1 through C5, etc.

There may be situations when it is desirable to fine tune the spectroscopic profile of the ICE so as to achieve enhanced resolution and/or accuracy. However, with conventional ICE configurations, once the ICE is designed and manufactured, such tuning is not possible since all the physical properties are already fixed.

Accordingly, there is a need in the art for methods by which to fine tune an existing ICE.

BRIEF DESCRIPTION OF THE DRAWINGS

FIGS. 2A and 2B show a front and side view of an ICE, respectively, which may be tilted according to illustrative embodiments of the present disclosure;

FIGS. 3A, 3B, 3C and 3D illustrate an ICE at various pivot angles;

DESCRIPTION OF ILLUSTRATIVE EMBODIMENTS

Illustrative embodiments and related methods of the present disclosure are described below as they might be employed in an optical computing device that alters the light incidence angle of an optical interference based ICE to thereby detect a plurality of sample characteristics. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, the present disclosure is directed to an optical computing device which manipulates the incidence angle of light interacting with the ICE, thereby enabling the detection of multiple sample characteristics. The effect of manipulating the light incidence angle is that the effective light path length through the ICE is altered, thus shifting the transmission spectral profile of the ICE. In certain illustrative embodiments, the change in spectral profile broadens the scope of the ICE from a single chemical component to multiple components, thus enabling the detecting of multiple sample characteristics. The alteration of the light incidence angle may be achieved in a variety of ways including, for example, a mechanism to tilt the ICE. In other embodiments, a mechanism moves the electromagnetic radiation source and optical transducer of the computing device to thereby alter the light incidence angle. In yet other embodiments, a processor selects an electromagnetic radiation source and optical transducer from an array to thereby alter the light incidence angle. Accordingly, fine tuning of existing ICEs may be accomplished using the illustrative embodiments of the present disclosure.

Figure 1:
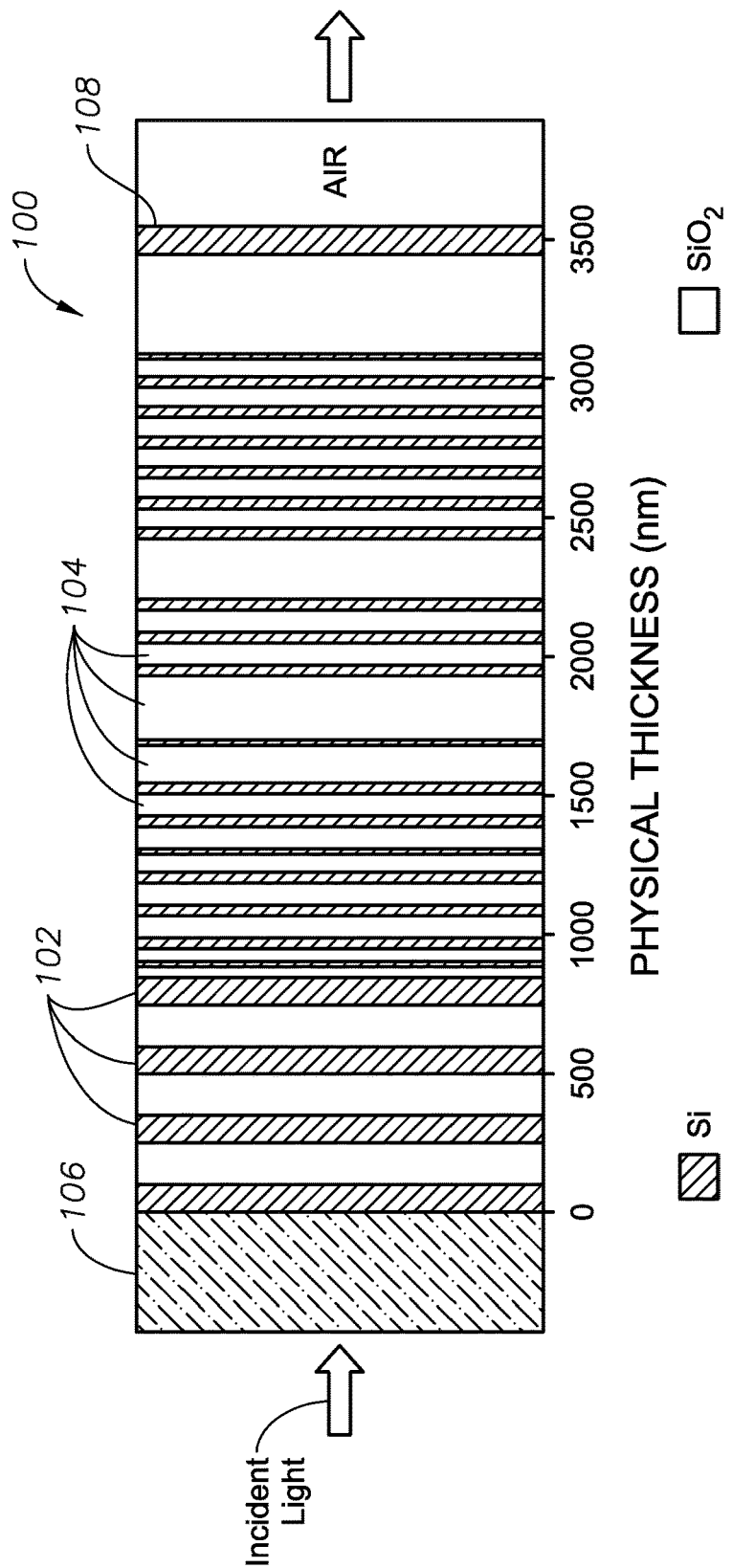
FIG. 1 illustrates a an ICE utilized in accordance to illustrative embodiments of the present disclosure.

Referring to FIG. 1, illustrated is an illustrative interference based ICE 100 which may be utilized in embodiments of the present disclosure. ICE 100 may include a plurality of alternating layers 102 and 104, such as, for example, silicon (Si) and quartz ($SiO_2$), respectively. Other non-limiting examples of layer materials include niobium, germanium and Germania, MgF, SiO, and other materials with high and low complex indices of refraction. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethalmethacrylate PMMA), polyvinylchloride (PVC), diamond, ceramics, etc., as known in the art. At the opposite end (e.g., opposite the optical substrate 106), the ICE 100 may include a layer 108 that is generally exposed to the environment of the device or installation. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The spectrum of interest of a given characteristic of a sample typically includes any number of different wavelengths. It should be understood that the illustrative ICE 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered to limit the present disclosure. Moreover, those skilled in the art will readily recognize that the materials that make up each layer 102, 104 may vary, depending on the application, cost of materials, and/or applicability of the material to the sample substance. For example, the layers 102, 104 may be made of, but are not limited to, silicon, quartz, germanium, water, combinations thereof, or other materials of interest.

In traditional ICE systems, light is incident on the ICE at a fixed angle in order to maintain the desired spectroscopic profile. In some ICE systems, incident light from a sample is normal to the surface of substrate 106, thus resulting in a set light path length through ICE 100. However, embodiments of the present disclosure manipulate the light incidence angle to thereby alter the light path length and the transmission spectral profile of the ICE. In a first illustrative embodiment, the ICE (positioned inside the optical computing device) is tilted to thereby change the light incidence angle. FIGS. 2A and 2B show a front and side view of an ICE, respectively, which may be tilted according to this illustrative embodiment. Here, an ICE 200 is secured to a plate 202 which holds ICE 200. Plate 202 may be metal, plastic or ceramic. A mechanism 206 is coupled to plate 202 to pivot plate 202 such that the light incidence angle is altered.

In this embodiment, ICE 200 has two pivot axes, A' and B'. Pivot axis A' is positioned along the edge of plate 202, while pivot axis B' is positioned at the center of plate 202 and ICE 200. Alternatively, however, the pivot axis and/or mechanism 206 may be located at other positions along plate 202. Mechanism 206 may be, for example, an actuator having a traveling piston. Alternatively, the actuator can be a piezoelectric device, a magnetostrictive device, a voice coil, a temperature controlled thermal actuator, a mechanical rotating screw. In yet other embodiments, plate 202 may be directly rotated by a stepping motor. For finer control, such actuators can be connected to a micrometer to yield highly precise control.

As previously mentioned, the effect of pivoting ICE 200 is to change the light incidence angle. As a result, the effective light path length through ICE 200 increases as the pivot angle is increased. FIGS. 3A, 3B, 3C and 3D illustrate ICE 200 to show the effect of pivoting. FIGS. 3A-3D shows ICE 200 pivoted at a 0° angle, 12.5° angle, 12° angle, and 45° angle, respectively. As light (represented by peak wavelength k) interacts with ICE 200, the effective path length is altered as a function of pivot angle. To further illustrate this point, and with reference to FIGS. 3A-3D and 4, let θ be the light incidence angle, and L be the path length at normal incidence with θ=0°. Thus, under pivoting situations, the effective path L' may be expressed as:

$$L'=L/(\cos(\theta)) \qquad \text{Eq. (1)},$$

Figure 4:
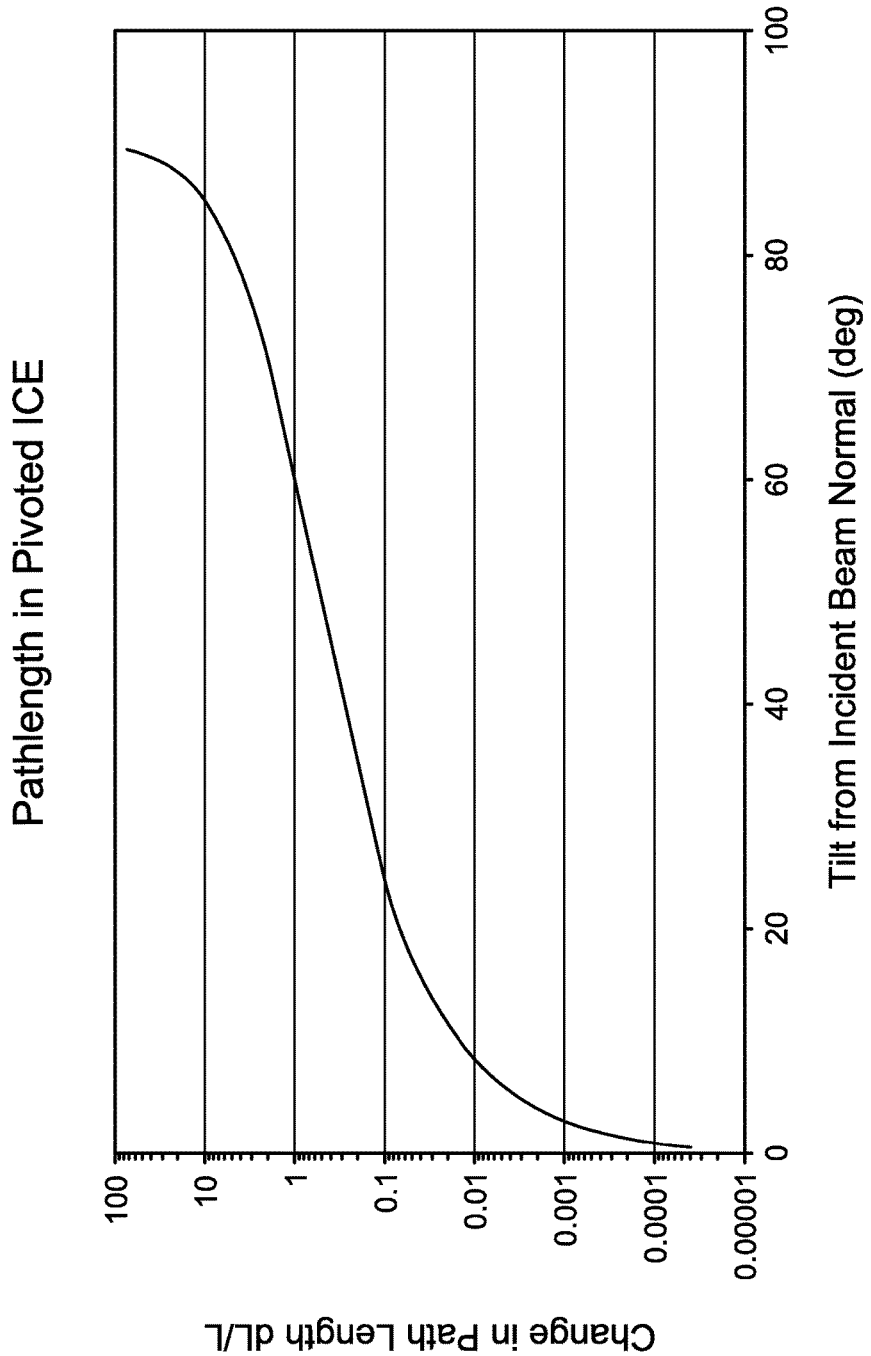
FIG. 4 is a graph showing the relationship between the changes in path length vs. changes in light incident angle as a result of pivoting the ICE from normal incidence.

FIG. 4 is a graph showing the relationship between the changes in path length vs. changes in incident angle as a result of pivoting the ICE from normal incidence.

The changes in path length for the cases shown in FIGS. 3A-3D are shown as numerical results listed in Table 1 below, which shows the path length L as a function of pivot angle θ. As can be seen, the effect of pivoting the ICE is to change the light incidence angle; hence, the effective light path length increases as the pivot angle θ is increased.

TABLE 1

| θ(°) | L | L' |
|---|---|---|
| 0 | 1 | 1.0 |
| 12.0 | 1 | 1.022341 |
| 12.5 | 1 | 1.02428 |
| 45.0 | 1 | 1.414214 |

Figure 5A:
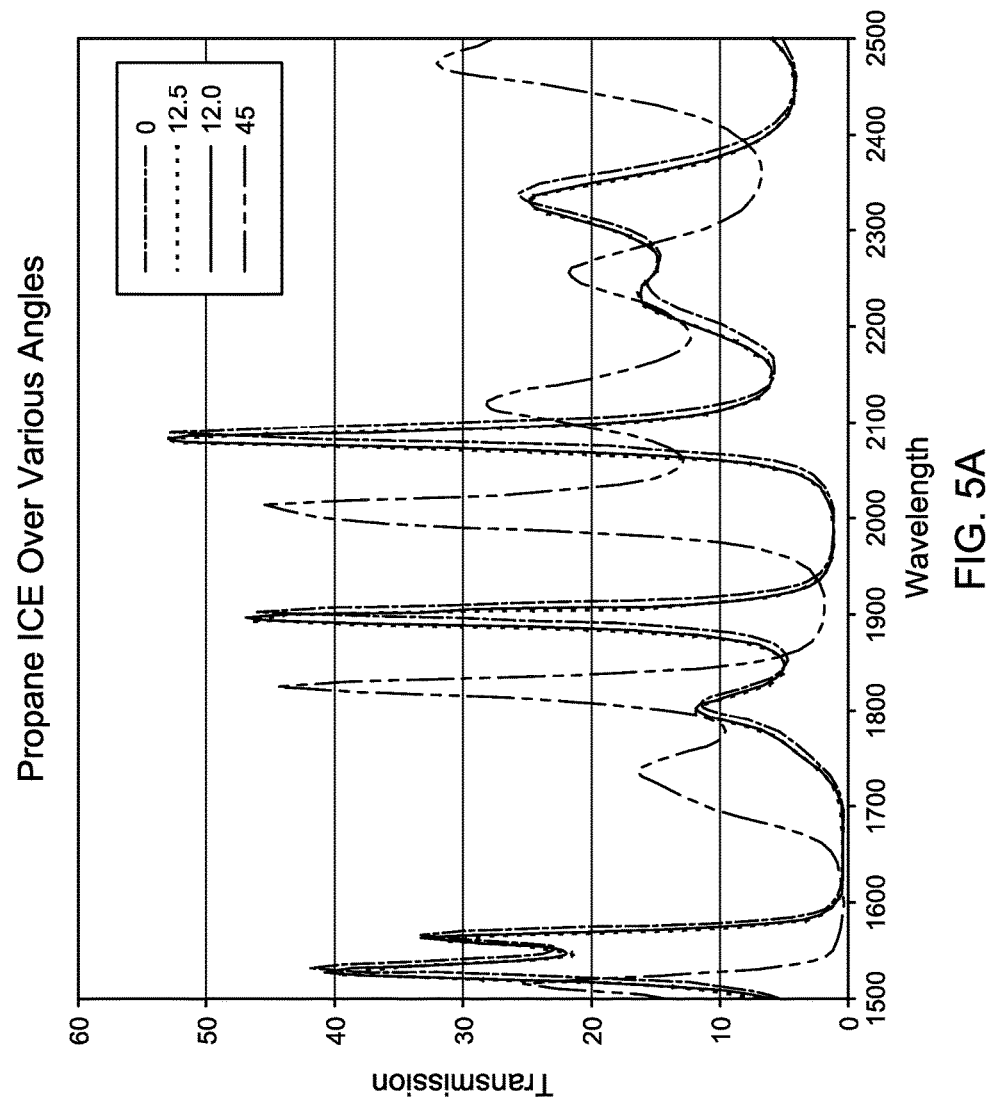
FIG. 5A shows the spectral shapes for an illustrative ICE at angles of 0°, 12.5°, 12° and 45°.
Figure 5B:
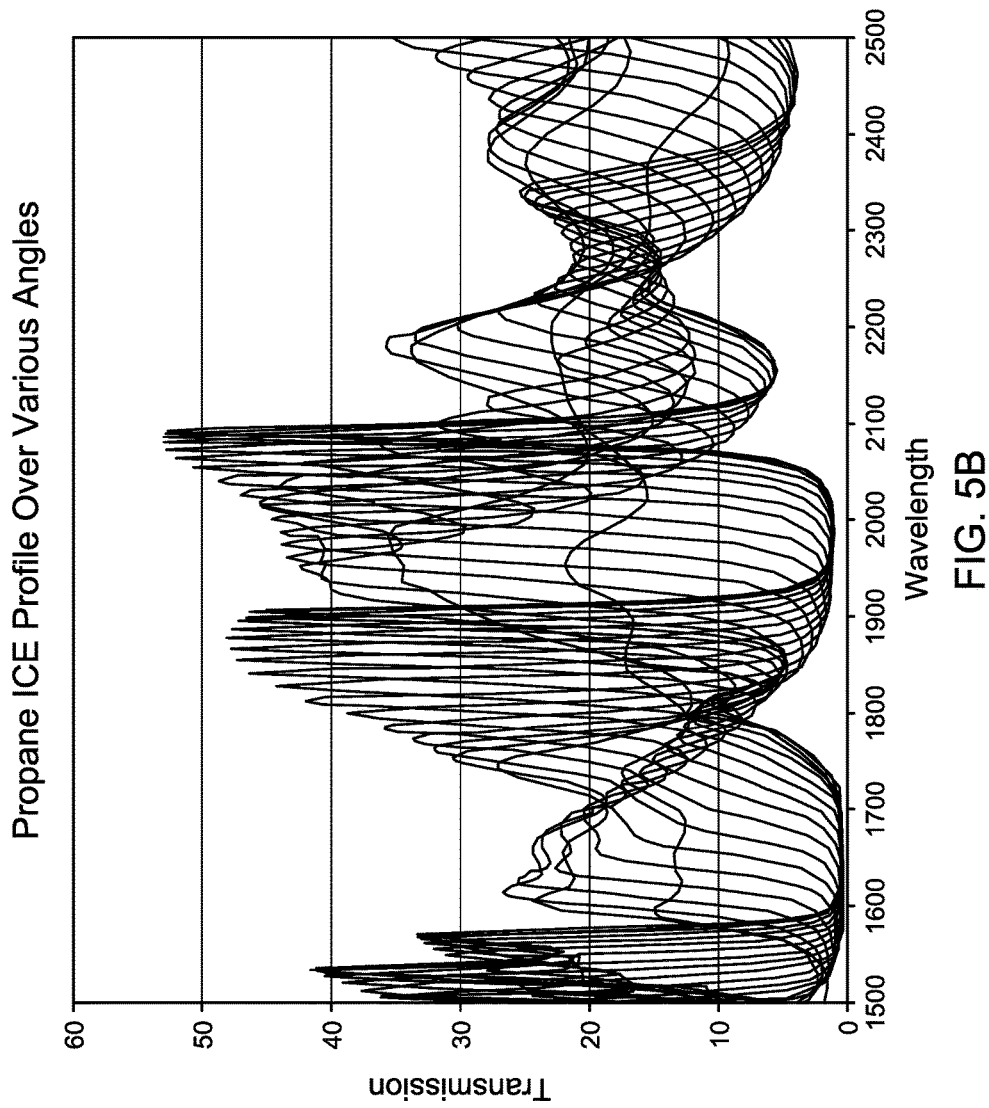
FIG. 5B shows the spectral shapes for an illustrative ICE at multiple angles.

The change in path length L' will lead to a shift in the spectral shape of the tilted ICE. The shift in the spectral shape may be described as a function of tilting angle and represented as:

$$\lambda(\theta) \approx \lambda_0 \sqrt{(1-(n_0/n_{\mathit{eff}})\sin^2\theta)} \qquad \text{Eq. (2),}$$

where $\lambda(\theta)$ is the peak wavelength at angle θ, $\lambda_0$ is the peak wavelength at normal incidence, $n_0$ is the index of the external medium (=1 for air), and $n_{\mathit{eff}}$ is the effective index of refraction of the ICE layers. As an example, the change in spectral shape for one ICE is calculated and plotted in FIGS. 5A and 5B. FIG. 5A shows the spectral shapes for an ICE at angles of 0°, 12.5°, 12° and 45°. FIG. 5B shows the spectral shapes for an ICE at various angles. Thus, it can be seen how the spectral shape changes as a result of manipulating the light incidence angle.

The effect of changing the path length leads to changes in the transmission spectral profile of the ICE. In certain illustrative embodiments of the present disclosure, the change in spectral profile broadens the performance of an ICE originally designed for the detection of a single chemical component to multiple components. One such example may be to use an ICE designed for propane ($C_3H_8$) to detect ethane ($C_2H_6$). In such an embodiment, one may calculate the relative standard error of prediction ("SEP") of using an ICE designed for methane to predict propane as a function of the tilt angle.

Figure 6:
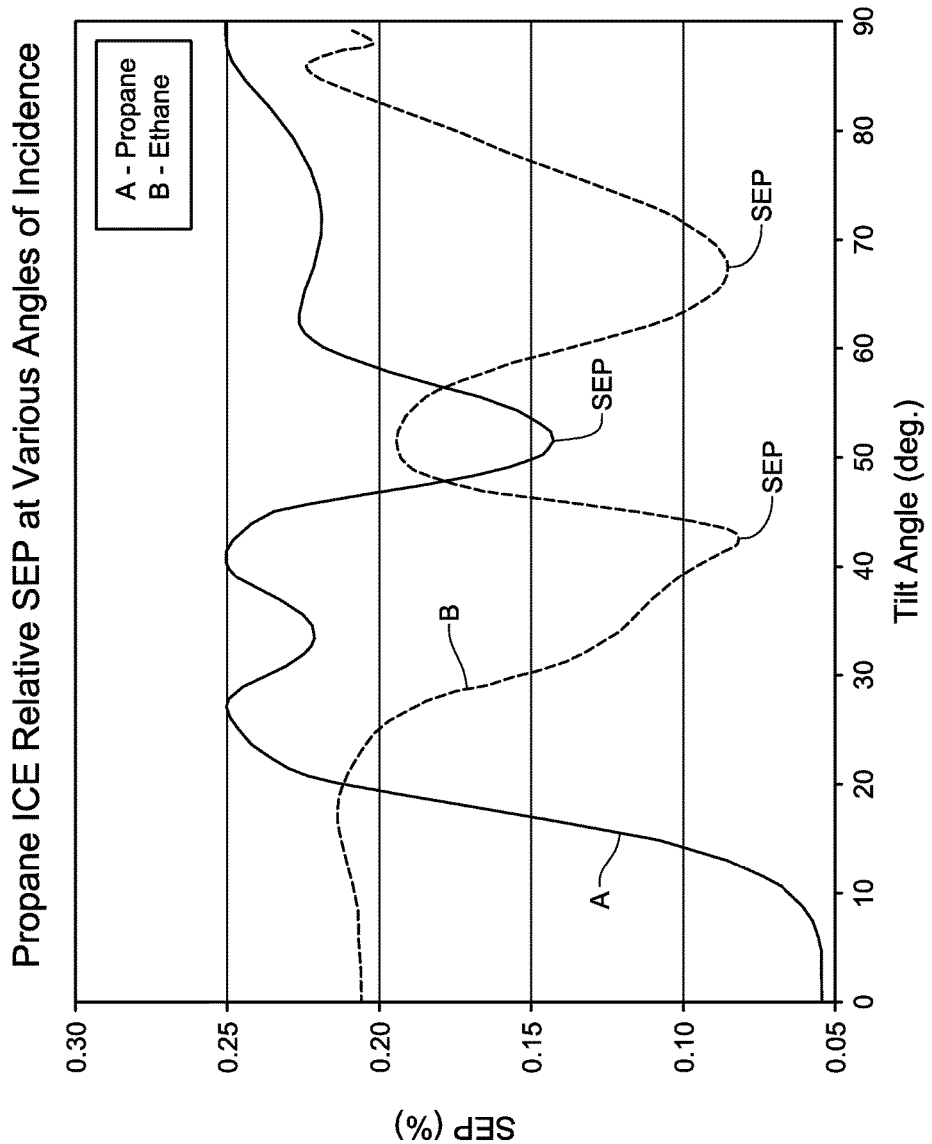
FIG. 6 is a graph plotting the standard error of prediction ("SEP") of using an illustrative ICE designed for propane to also detect ethane.

To further illustrate this point, FIG. 6 is a graph plotting the SEP of using an ICE designed for propane to detect ethane. As shown, the propane ICE is most predictive of propane at/near the normal incidence angle (i.e., tilt angle 0°), where the relative SEP "A" is near 0.05. However, note that at tilt angles of 43° and 67°, the propane ICE is also predictive for ethane with relative errors of about 0.07. Accordingly, during operation of an illustrative computing device utilizing this propane ICE, the device may first detect a concentration of propane while the light incidence angle is normal. Thereafter, the light incidence angle may be changed to 43°, whereby a concentration of ethane may then be detected. Alternatively, by rocking the ICE back and forth over a small angle, the accuracy and resolution of chemical component detection may be enhanced in other embodiments. This is advantageous when detecting components that have similar, but minute differences in their spectral responses, such as in differentiating organic compounds having high carbon numbers.

Figure 7A:
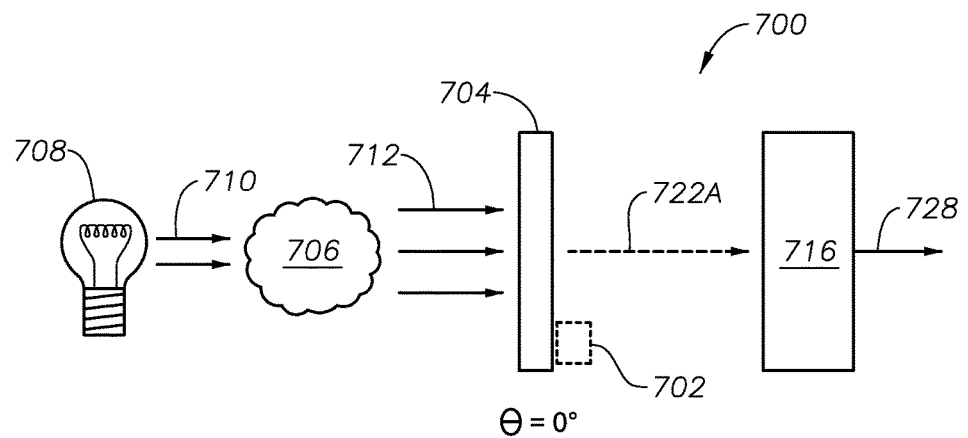
FIGS. 7A and 7B are block diagrams of an optical computing device utilizing an actuator to tilt the ICE to achieve a light incidence angle of 0° and 45°, respectively, according to an illustrative embodiment of the present disclosure.

In light of the foregoing theory, various illustrative embodiments of the present disclosure will now be described. As previously described, the optical computing devices of the present disclosure utilize various mechanisms to alter the light incidence angle. FIG. 7A is a block diagram of an illustrative architecture of an optical computing device 700 utilizing an actuator to tilt the ICE. An electromagnetic radiation source 708 may be configured to emit or otherwise generate electromagnetic radiation 710. As understood in the art, electromagnetic radiation source 708 may be any device capable of emitting or generating electromagnetic radiation. For example, electromagnetic radiation source 708 may be a light bulb, light emitting device, laser, blackbody, photonic crystal, or X-Ray source, natural luminescence, etc. In one embodiment, electromagnetic radiation 710 may be configured to optically interact with the sample 706 to thereby generate sample-interacted light 712. Sample 706 may be any desired sample, such as, for example, a fluid (liquid or gas), solid substance or material such as, for example, hydrocarbons or food products. While FIG. 7 shows electromagnetic radiation 710 as passing through or incident upon the sample 706 to produce sample-interacted light 712 (i.e., transmission or fluorescent mode), it is also contemplated herein to reflect electromagnetic radiation 710 off of the sample 706 (i.e., reflectance mode), such as in the case of a sample 706 that is translucent, opaque, or solid, and equally generate the sample-interacted light 712.

After being illuminated with electromagnetic radiation 710, sample 706 containing an analyte of interest (a characteristic of the sample) produces an output of electromagnetic radiation (sample-interacted light 712, for example). As previously described, sample-interacted light 712 also contains spectral information of the sample used to determine one or more characteristics of sample 706. Although not specifically shown, one or more spectral elements may be employed in optical computing device 700 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Although not shown, optical computing device 700 may be coupled to a remote power supply, while in other embodiments optical computing device 700 comprises an on-board battery. Optical computing device 700 may also comprise a signal processor (not shown), communications module (not shown) and other circuitry necessary to achieve the objectives of the present disclosure, as will be understood by those ordinarily skilled in the art having the benefit of this disclosure. It will also be recognized that the software instructions necessary to carry out the objectives of the present disclosure may be stored within storage located on optical computing device 700 or loaded into that storage from a CD-ROM or other appropriate storage media via wired or wireless methods.

Alternatively, however, the processor may be located remotely from optical computing device 700. In such embodiments, a communications link provides a medium of communication between the processor and optical computing device 700. The communications link may be a wired link, such as, for example, a fiber optic cable. Alternatively, however, the link may be a wireless link. In certain illustrative embodiments, the signal processor controls operation of optical computing device 700 (including the tilt angle of ICE 704). Optical computing device 500 may also include a transmitter and receiver (transceiver, for example) (not shown) that allows bi-directional communication over a communications link in real-time. In certain illustrative embodiments, optical computing device 700 will transmit all or a portion of the sample characteristic data to a remote processor for further analysis. However, in other embodiments, such analysis is completely handled by optical computing device 700 and the resulting data is then transmitted remotely for storage or subsequent analysis. In either embodiment, the processor handling the computations may, for example, analyze the characteristic data, or perform simulations based upon the characteristic data, as will be readily understood by those ordinarily skilled in the art having the benefit of this disclosure.

Still referring to the illustrative embodiment of FIG. 7A, sample-interacted light 712 is then directed to ICE 704. An actuator 702 is coupled to ICE 704 in order to tilt ICE 704 to the desired tilt angle. In this example, ICE 704 is designed to correspond to a first chemical system having one or more components (spectral data representing a first characteristic and first interferents associated with the first chemical system) at the pivot angle θ=0° (i.e., first incidence angle). Therefore, the chemical systems may comprise, for example, a single characteristic in different fluids, a single characteristic having differing ranges in the different fluids, or different characteristics.

Nevertheless, sample-interacted light 712 then optically-interacts with ICE 704 to produce first optically interacted light 722A which corresponds to a characteristic of the first chemical system. First optically-interacted light is then directed to detector 716 may be any device capable of detecting electromagnetic radiation, and may be generally characterized as an optical transducer. For example, detector 716 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art. Detector 716 is further configured to produce an output signal 728 in the form of a voltage that corresponds to the characteristic of the sample 506. In at least one embodiment, output signal 728 produced by detector 716 and the characteristic concentration of the sample 706 may be directly proportional. In other embodiments, the relationship may be a polynomial function, an exponential function, and/or a logarithmic function.

Although not shown, optical computing device 700 may also include a second detector to detect a normalizing signal, as will be understood by those ordinarily skilled in the art having the benefit of this disclosure. Electromagnetic radiation propagating through computing device 700 may include a variety of radiating deviations stemming from electromagnetic radiation source 708 such as, for example, intensity fluctuations in the electromagnetic radiation, interferent fluctuations (for example, dust or other interferents passing in front of the electromagnetic radiation source), combinations thereof, or the like. Thus, the second detector detects such radiating deviations as well. In an alternative embodiment, the second detector may be arranged to receive a portion of the sample-interacted light 712, and thereby compensate for electromagnetic radiating deviations stemming from the electromagnetic radiation source 708. In yet other embodiments, the second detector may be arranged to receive a portion of electromagnetic radiation 710, and thereby likewise compensate for electromagnetic radiating deviations stemming from the electromagnetic radiation source 708. Those ordinarily skilled in the art having the benefit of this disclosure will realize there are a variety of design alterations which may be utilized in conjunction with embodiments of the present disclosure.

Although not shown in FIG. 7A, in certain illustrative embodiments, detector 716 may be communicably coupled to a signal processor (not shown) on-board optical computing device 700 such that signal 728 and the normalizing signal indicative of electromagnetic radiating deviations may be provided or otherwise conveyed thereto. The signal processor may then be configured to computationally combine the normalizing signal with output signal 728 to provide a more accurate determination of the one or more characteristics of sample 706. However, in the embodiment of FIG. 7A, the signal processor would be coupled to the one detector. Nevertheless, in those embodiments using two detectors, for example, the signal processor computationally combines the normalizing signal with output signal 728 via principal component analysis techniques such as, for example, standard partial least squares which are available in most statistical analysis software packages (for example, XL Stat for MICROSOFT® EXCEL® the UNSCRAMBLER® from CAMO Software and MATLAB® from MATHWORKS®), as will be understood by those ordinarily skilled in the art having the benefit of this disclosure. Thereafter, the resulting data is then transmitted to the processor for further operations to determine the characteristic of sample 706 for which ICE 704 was designed.

Figure 7B:
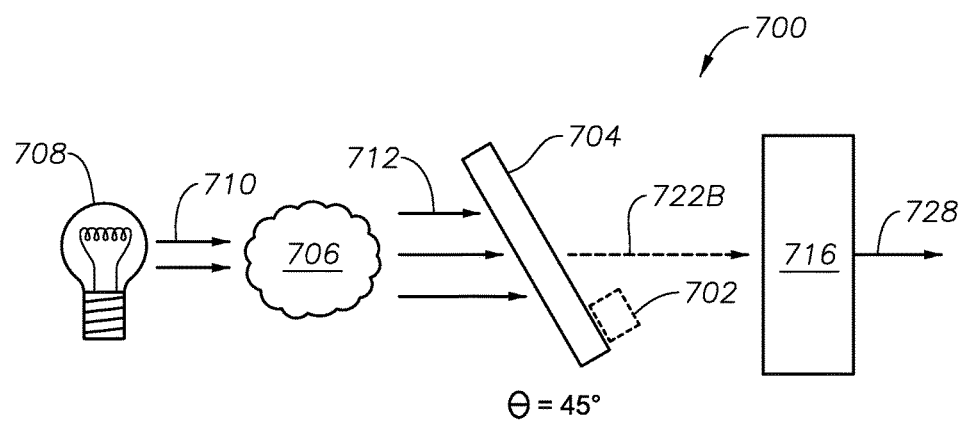

FIG. 7B is a block diagram of optical computing 700 with ICE 704 being tilted to a pivot angle 45°. In this illustrative embodiment, after the first optically-interacted light 722A has been produced at the pivot angle of θ=0°, the processor sends a signal to actuator 702 to tilt ICE 704 to a pivot angle of 45°. The resulting light incidence angle (i.e., second light incidence angle) of sample-interacted light 712 causes ICE 704 to produce a second optically-interacted light 722B which corresponds to a second chemical system having one or more components (spectral data representing a second characteristic and second interferents associated with the second chemical system). In other words, actuator 702 has changed the first light incidence angle to a second light incidence angle. As previously described, the characteristic and/or interferents of the second chemical system may be the same or different from those of the first chemical system. Thus, if the second chemical system is different, optically-interacted light 722B will correspond to a characteristic different from that of optically-interacted light 722A; this is because, as previously described, ICE 702 has a first spectral profile at the first light incidence angle, and a second spectral profile at the second light incidence angle. Therefore, for example, the characteristic of optically-interacted light 722A may correspond to a concentration of methane, while the characteristic of optically-interacted light 722B may correspond to a concentration of propane. Thereafter, optically-interacted light 722B is directed on to detector 716 for further processing as previously described.

As previously described, actuator 702 may be a temperature-controlled actuator. In such embodiments, for example, the pivot angle of ICE 704 may be changed in response to a temperature change, as certain temperature fluctuations can reduce the accuracy of the ICE prediction. By utilizing a temperature-controlled actuator, the light incidence angle can be altered to compensate for the temperature fluctuation, thus maintaining the integrity of the ICE performance.

Figure 8:
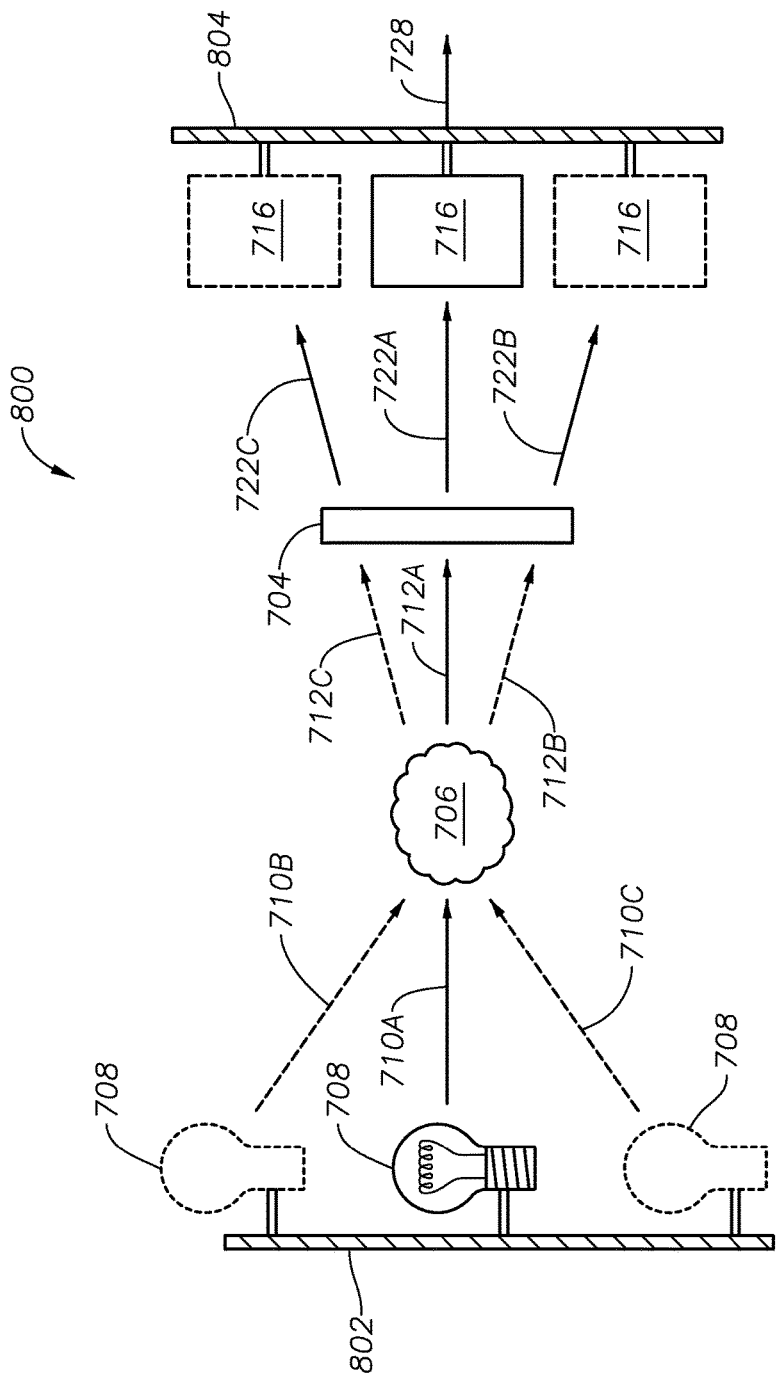
FIG. 8 is a block diagram of an optical computing device utilizing a mechanism to move an electromagnetic source and optical transducer to alter the light incidence angle, according to an illustrative embodiment of the present disclosure.

FIG. 8 is a block diagram of an optical computing device utilizing a mechanism to move the electromagnetic source and optical transducer to alter the light incidence angle, according to an alternate embodiment of the present disclosure. Optical computing device 800 is somewhat similar to optical computing device 700 and, therefore, may be best understood with reference thereto, where like numerals indicate like elements. However, optical computing device 800 includes a mechanism 802 and 804 to move electromagnetic radiation source 708 and detector 716, respectively, thereby altering the light incidence angle. Mechanisms 802 and 804 may be, for example linear actuators. Mechanisms 802,804 are coupled to the processor (not shown), which controls the light incidence angle by causing mechanisms 802,804 to position electromagnetic radiation source 708 and detector 716 as needed.

During operation of optical computing device 800, electromagnetic radiation source 708 may first be positioned to generate electromagnetic radiation 710A, which optically interacts with sample 706 to produce sample-interacted light 712A. Sample-interacted light 712A then transmits through ICE 704 at a first light incidence angle (normal angle), thus generating optically-interacted light 722A which corresponds to characteristic for which ICE 704 was designed at normal incidence. Optically-interacted light 722A is then directed on to detector 716 (which has been positioned by the processor, via mechanism 804, to receive light 722A). Output signal 728 is then produced and processed to determine the characteristic as previously described.

Subsequently, the processor may send a signal to mechanisms 802,804 to move electromagnetic radiation source 708 and detector 716 to cause a change in the light incidence angle. Thus, for example, this movement can result in the positioning of electromagnetic radiation source 708 to generate electromagnetic radiation 710B, which optically interacts with sample 706 to produce sample-interacted light 712B, having a second light incidence angle different from that of optically-interacted light 712A. The light incidence angle of sample-interacted light 712B would be selected to predict another characteristic of sample 706, as previously described. The optically-interacted light 722B is then generated and directed onto detector 716, which has been positioned to receive the light and generate output signal 728.

Thereafter, electromagnetic radiation source 708 and detector 716 may again be moved in like-manner to thereby produce electromagnetic radiation 710 with interacts with sample 706 to produce sample-interacted light 712C. Sample-interacted light 712 may have a third light incidence angle different from that of sample-interacted lights 712A and 712B, thus allowing the detection of a third characteristic different from the previous two. The resulting optically-interactive light 712C is then directed onto to 716, which has been positioned accordingly to produce output signal 728. In alternative embodiments, however, any number of light incidence angles may be achieved using this embodiment, thus allowing ICE 704 to detect multiple characteristics of sample 706.

Figure 9:
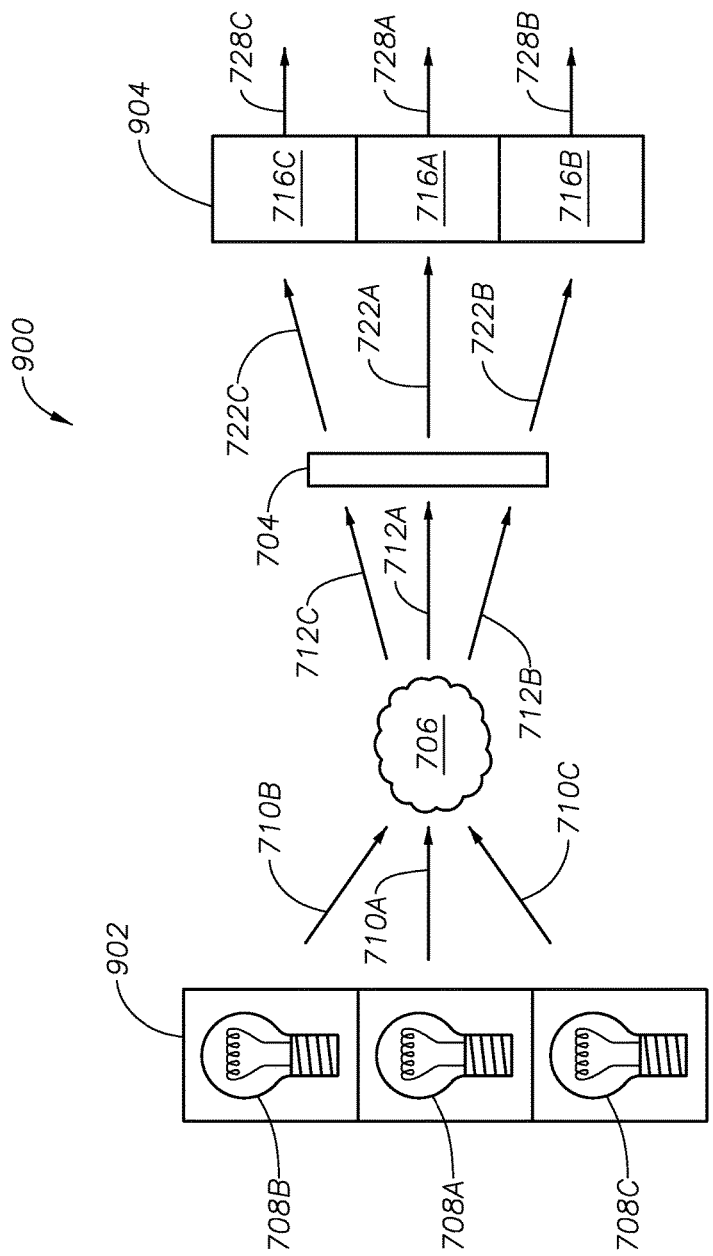
FIG. 9 is a block diagram of an optical computing device utilizing an array of electromagnetic sources and optical transducers to alter the light incidence angle, according to an illustrative embodiment of the present disclosure.

FIG. 9 is a block diagram of an optical computing device utilizing an array of electromagnetic sources and optical transducers to alter the light incidence angle, according to an alternate embodiment of the present disclosure. Optical computing device 900 is somewhat similar to optical computing device 700 and, therefore, may be best understood with reference thereto, where like numerals indicate like elements. However, optical computing device 900 includes an electromagnetic radiation source array 902 and detector array 904, each communicably coupled to the processor (not shown). During operation, the processor selects an electromagnetic radiation source 708 and detector 716 to thereby alter the light incidence angle as desired. For example, electromagnetic radiation source 708A and detector 716A may first be selected. Electromagnetic radiation 710A is then generated as caused to interact with sample 706 to produce sample-interacted light 712A, which optically interacts with ICE 704 at a first light incidence angle (normal angle, for example). Optically-interacted light 722A, which corresponds to a first characteristic of sample 706, is thereafter produced and directed to detector 716A. Output signal 728A is thereafter produced and processed to determine the first characteristic.

Thereafter, the processor may then select electromagnetic radiation source 708B and detector 716B. Electromagnetic radiation 710B is then generated as caused to interact with sample 706 to produce sample-interacted light 712B, which optically interacts with ICE 704 at a second light incidence angle. Optically-interacted light 722B, which corresponds to a second characteristic of sample 706, is thereafter produced and directed to detector 716B. Output signal 728B is thereafter produced and processed to determine the second characteristic.

Thereafter, the processor may then select electromagnetic radiation source 708C and detector 716C. Electromagnetic radiation 710C is then generated as caused to interact with sample 706 to produce sample-interacted light 712C, which optically interacts with ICE 704 at a third light incidence angle different from that of sample-interacted lights 712A and 712B. Optically-interacted light 722C, which corresponds to a third characteristic of sample 706, is thereafter produced and directed to detector 716C. Output signal 728C is thereafter produced and processed to determine the third characteristic. Optical computing device 900 is especially useful in that it includes no moving parts, thus providing increased reliability.

The multi-characteristic ICEs and optical computing devices described herein may be utilized in a variety of environments. Such environments may include, for example, a reservoir material interrogating system used in a downhole well or completion applications. Other environments may include those as diverse as those associated with surface and undersea monitoring, satellite or drone surveillance, pipeline monitoring, or even sensors transiting a body cavity such as a digestive tract. Within those environments, the optical computing devices are utilized to detect various compounds or characteristics in order to monitor, in real time, various phenomena occurring within the environment.

Embodiments described herein further relate to any one or more of the following paragraphs:

1. An optical computing device, comprising electromagnetic radiation that optically interacts with a sample to produce sample-interacted light; an Integrated Computational Element ("ICE") positioned to optically interact with the sample-interacted light at a first light incidence angle to thereby produce a first optically-interacted light that corresponds to a first chemical system having one or more components; a mechanism to change the first light incidence angle to a second light incidence angle to thereby produce a second optically-interacted light that corresponds to a second chemical system having one or more components; and an optical transducer positioned to receive the first and second optically-interacted lights to thereby generate signals that are utilized to determine characteristics of the sample.

2. An optical computing device as defined in paragraph 1, wherein the ICE has a first spectral profile at the first light incidence angle; and the ICE has a second spectral profile at the second light incidence angle.

3. An optical computing device as defined in paragraphs 1 or 2, wherein the components of the first chemical system are a set of spectral data representing a first characteristic and first interferents associated with the first chemical system; and the components of the second chemical system are a set of spectral data representing the first characteristic and second interferents associated with the second chemical system, the second interferents being different from the first interferents.

4. An optical computing device as described in any of paragraphs 1-3, wherein the components of the first chemical system are a set of spectral data representing a first characteristic and interferents associated with the first chemical system; and the components of the second chemical system are a set of spectral data representing a second characteristic and interferents associated with the second chemical system, the second characteristic being different from the first characteristic.

5. An optical computing device as defined in any of paragraphs 1-4, wherein the mechanism comprises an actuator coupled to the ICE to thereby pivot the ICE, thereby changing the first light incidence angle to the second light incidence angle.

6. An optical computing device as defined in any of paragraphs 1-5, wherein the actuator is a temperature-controlled thermal actuator.

7. An optical computing device as defined in any of paragraphs 1-6, wherein the mechanism comprises a mechanism to move a source of the electromagnetic radiation and the optical transducer such that the first light incidence angle is changed to the second light incidence angle.

8. An optical computing device as defined in any of paragraphs 1-7, wherein the mechanism comprises an array of electromagnetic sources that produce the electromagnetic radiation; an array of optical transducers positioned to receive the optically interacted light; and a processor to select one of the electromagnetic sources and one of the optical transducers such that the first light incidence angle is changed to the second light incidence angle.

9. An optical computing device as defined in any of paragraphs 1-8, wherein the optical computing device forms part of a reservoir material interrogating system.

10. An optical computing method, comprising optically interacting electromagnetic radiation with a sample to produce sample-interacted light; optically interacting the sample-interacted light with an Integrated Computational Element ("ICE") at a first light incidence angle to produce a first optically-interacted light that corresponds to a first chemical system having one or more components; changing the first light incidence angle to a second light incidence angle to thereby produce a second optically-interacted light that corresponds to a second chemical system having one or more components; and optically interacting the first and second optically-interacted lights with an optical transducer to thereby generate signals utilized to determine characteristics of the sample.

11. An optical computing method as defined in paragraphs 10, wherein: producing the first optically-interacted light comprises producing a first spectral profile of the first optically-interacted light; and producing the second optically-interacted light comprises producing a second spectral profile of the second optically-interacted light.

12. An optical computing method as defined in paragraphs 10-11, wherein changing the first light incidence angle comprises pivoting the ICE to thereby change the first light incidence angle to the second light incidence angle.

13. An optical computing method as defined in any of paragraphs 10-12, further comprising pivoting the ICE in response to temperature.

14. An optical computing method as defined in any of paragraphs 10-13, further comprising rotating the ICE back and forth between the first and second light incidence angles.

15. An optical computing method as defined in any of paragraphs 10-14, wherein changing the first light incidence angle comprising moving a source of the electromagnetic radiation and optical transducer such that the first light incidence angle is changed to the second light incidence angle.

16. An optical computing method as defined in any of paragraphs 10-15, wherein changing the first light incidence angle comprises selecting one of an array of electromagnetic sources and one of an array of optical transducers to thereby change the first light incidence angle to the second light incidence angle.

17. An optical computing method as defined in any of paragraphs 10-16, further comprising determining at least two different characteristics using the ICE.

18. An optical computing method as defined in any of paragraphs 10-17, wherein the method is performed in a downhole environment.

19. An optical computing method, comprising altering a light incidence angle of sample-interacted light; optically interacting the sample-interacted light with an Integrated Computational Element ("ICE") at the altered light incidence angle to produce optically-interacted light that corresponds to a characteristic of the sample; and determining the characteristic of the sample.

20. An optical computing method as defined in paragraph 19, wherein altering the light incidence angle comprises one or more of tilting the ICE; moving a light source utilized to create the sample-interacted light; moving an optical transducer that receives the optically-interacted light; selecting one of an array of light sources utilized to create the sample-interacted light; and selecting one of an array of optical transducers that receive the optically-interacted light.

Moreover, the methodologies described herein may be embodied within a system comprising processing circuitry to implement any of the methods, or a in a computer-program product comprising instructions which, when executed by at least one processor, causes the processor to perform any of the methods described herein.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. An optical computing device, comprising:
an electromagnetic radiation source which produces electromagnetic radiation that optically interacts with a sample to produce sample-interacted light;
an Integrated Computational Element ("ICE") that corresponds to a first chemical system having one or more components and a second chemical system having one or more components different from the one or more components of the first chemical system, the ICE being positioned to optically interact with the sample-interacted light at a first light incidence angle to thereby produce a first optically-interacted light that corresponds to the first chemical system;
a mechanism to change the first light incidence angle to a second light incidence angle to thereby produce a second optically-interacted light that corresponds to the second chemical system; and an optical transducer positioned to receive the first and second optically-interacted lights to thereby generate signals that are utilized to determine characteristics of the sample.

2. The optical computing device as defined in claim 1, wherein:
the ICE has a first spectral profile at the first light incidence angle; and
the ICE has a second spectral profile at the second light incidence angle.

3. The optical computing device as defined in claim 1, wherein:
the components of the first chemical system are a set of spectral data representing a first characteristic and first interferents associated with the first chemical system; and
the components of the second chemical system are a set of spectral data representing the first characteristic and second interferents associated with the second chemical system, the second interferents being different from the first interferents.

4. The optical computing device as described in claim 1, wherein:
the components of the first chemical system are a set of spectral data representing a first characteristic and interferents associated with the first chemical system; and
the components of the second chemical system are a set of spectral data representing a second characteristic and interferents associated with the second chemical system, the second characteristic being different from the first characteristic.

5. The optical computing device as defined in claim 1, wherein the mechanism comprises an actuator coupled to the ICE to thereby pivot the ICE, thereby changing the first light incidence angle to the second light incidence angle.

6. The optical computing device as defined in claim 5, wherein the actuator is a temperature-controlled thermal actuator.

7. The optical computing device as defined in claim 1, wherein the mechanism comprises a mechanism to move the electromagnetic radiation source and the optical transducer such that the first light incidence angle is changed to the second light incidence angle.

8. The optical computing device as defined in claim 1, wherein the mechanism comprises:
an array of electromagnetic sources that produce the electromagnetic radiation;
an array of optical transducers positioned to receive the optically interacted light; and
a processor to select one of the electromagnetic sources and one of the optical transducers such that the first light incidence angle is changed to the second light incidence angle.

9. The optical computing device as defined in claim 1, wherein the optical computing device forms part of a reservoir material interrogating system.

10. An optical computing method, comprising:
optically interacting electromagnetic radiation with a sample to produce sample-interacted light;
optically interacting the sample-interacted light with an Integrated Computational Element ("ICE") at a first light incidence angle to produce a first optically-interacted light that corresponds to a first chemical system having one or more components;
changing the first light incidence angle to a second light incidence angle to thereby produce a second optically-interacted light that corresponds to a second chemical system having one or more components different from the one or more components of the first chemical system; and
optically interacting the first and second optically-interacted lights with an optical transducer to thereby generate signals utilized to determine characteristics of the sample.

11. The optical computing method as defined in claim 10, wherein:
producing the first optically-interacted light comprises producing a first spectral profile of the first optically-interacted light; and
producing the second optically-interacted light comprises producing a second spectral profile of the second optically-interacted light.

12. The optical computing method as defined in claim 10, wherein changing the first light incidence angle comprises pivoting the ICE to thereby change the first light incidence angle to the second light incidence angle.

13. The optical computing method as defined in claim 12, further comprising pivoting the ICE in response to temperature.

14. The optical computing method as defined in claim 12, further comprising rotating the ICE back and forth between the first and second light incidence angles.

15. The optical computing method as defined in claim 10, wherein changing the first light incidence angle comprising moving a source of the electromagnetic radiation and optical transducer such that the first light incidence angle is changed to the second light incidence angle.

16. The optical computing method as defined in claim 10, wherein changing the first light incidence angle comprises selecting one of an array of electromagnetic sources and one of an array of optical transducers to thereby change the first light incidence angle to the second light incidence angle.

17. The optical computing method as defined in claim 10, further comprising determining at least two different characteristics using the ICE.

18. The optical computing method as defined in claim 10, wherein the method is performed in a downhole environment.

19. An optical computing method, comprising:
altering a light incidence angle of sample-interacted light to produce a plurality of sample-interacted lights, each sample interacted light corresponding to a different light incidence angle;
optically interacting the plurality of sample-interacted lights with a single Integrated Computational Element ("ICE") at the altered light incidence angles to produce a plurality of optically-interacted lights that correspond to a plurality of characteristics of the sample; and
determining the plurality of characteristics of the sample.

20. The optical computing method as defined in claim 19, wherein altering the light incidence angle comprises one or more of:
tilting the ICE;
moving a light source utilized to create the sample-interacted lights;
moving an optical transducer that receives the optically-interacted lights;
selecting one of an array of light sources utilized to create the sample-interacted lights; and
selecting one of an array of optical transducers that receive the optically-interacted lights.

* * * * *